(12) United States Patent
Takamatsu et al.

(10) Patent No.: US 7,884,257 B2
(45) Date of Patent: *Feb. 8, 2011

(54) METHOD FOR PRODUCING ETHYLENE AND PROPYLENE

(75) Inventors: Yoshikazu Takamatsu, Tokyo (JP); Kouji Nomura, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 393 days.

This patent is subject to a terminal disclaimer.

(21) Appl. No.: 12/066,991

(22) PCT Filed: Sep. 14, 2006

(86) PCT No.: PCT/JP2006/318296

§ 371 (c)(1),
(2), (4) Date: Mar. 14, 2008

(87) PCT Pub. No.: WO2007/032447

PCT Pub. Date: Mar. 22, 2007

(65) Prior Publication Data

US 2009/0182184 A1 Jul. 16, 2009

(30) Foreign Application Priority Data

Sep. 16, 2005 (JP) ............................ P2005-270322

(51) Int. Cl.
*C07C 4/06* (2006.01)
(52) U.S. Cl. .................... 585/651; 585/653; 208/73; 208/76; 208/113; 208/120.15
(58) Field of Classification Search ................. 585/651, 585/653; 208/73, 76, 113, 120.15; 502/64, 502/71, 77
See application file for complete search history.

(56) References Cited

U.S. PATENT DOCUMENTS 6,307,117 B1  10/2001  Tsunoda et al.

FOREIGN PATENT DOCUMENTS

| KR | 2001-0024221 A | 3/2001 |
| WO | WO-96/13331 A1 | 5/1996 |
| WO | WO-00/10948 A1 | 3/2000 |
| WO | WO-2004/072002 A1 | 8/2004 |
| WO | WO-2006/009099 A1 | 1/2006 |

OTHER PUBLICATIONS

English translation of Korean Office Action issued on Nov. 25, 2009 in corresponding Korean Application No. 10-2008-7006307.

*Primary Examiner*—Tam M Nguyen
(74) *Attorney, Agent, or Firm*—Birch, Stewart, Kolasch & Birch, LLP

(57) ABSTRACT

The invention is to provide a catalyst for long-term, high-yield and stable production of ethylene and propylene in an efficient and simple method of catalytic conversion from a hydrocarbon material. The invention relates to a method for producing ethylene and propylene by contacting a hydrocarbon material that contains an olefin having from 4 to 12 carbon atoms in an amount of at least 20% by weight, with a zeolite-containing shaped catalyst satisfying the following requirements (1) to (4), in a reactor for catalytic conversion of that olefin:

(1) the zeolite is an intermediate pore-size zeolite having a pore size of from 5 to 6.5 angstroms,
(2) the zeolite does not substantially contain a proton,
(3) the zeolite contains at least one metal selected from the group consisting of metals belonging to the Group IB of the Periodic Table,
(4) the zeolite has a silica/alumina molar ratio ($SiO_2/Al_2O_3$ molar ratio) of from 800 to 2,000.

9 Claims, 1 Drawing Sheet

[Fig. 1]

METHOD FOR PRODUCING ETHYLENE AND PROPYLENE

TECHNICAL FIELD

The present invention relates to a method for producing ethylene and propylene through catalytic conversion from a hydrocarbon material. More precisely, the invention relates to a method for producing ethylene and propylene by contacting a hydrocarbon material that contains at least one olefin having from 4 to 12 carbon atoms in an amount of at least 20% by weight with a zeolite-containing shaped catalyst in a reactor to thereby carry out catalytic conversion of the at least one olefin having from 4 to 12 carbon atoms.

BACKGROUND ART

Many methods are known for catalytic conversion from an olefin-containing hydrocarbon material with a zeolite-containing catalyst; and there are many reports relating to methods for producing ethylene and propylene through catalytic conversion from an olefin-containing hydrocarbon material with a zeolite-containing catalyst.

However, efficient, stable and long-lasting production of ethylene and propylene through catalytic conversion from an olefin-containing hydrocarbon material with a zeolite-containing catalyst was difficult for the following reasons.

Ethylene and propylene are intermediates in conversion from olefins to aromatic hydrocarbons in the presence of a zeolite catalyst, and they are converted into aromatic hydrocarbons through successive reaction. Accordingly, in case where ethylene and propylene are produced through catalytic conversion from an olefin-containing hydrocarbon material with a zeolite-containing catalyst, the activity of the catalyst and the reaction condition must be severely controlled for obtaining the product at high yield. Specifically, when the catalyst activity is too high or when the contact time is too long, then the produced ethylene and propylene would be converted into aromatic hydrocarbons through successive reaction. On the contrary, when the catalyst activity is too low or when the contact time is too short, then the yield of ethylene and propylene would be low.

On the other hand, olefins are highly reactive, and when an olefin-containing hydrocarbon material is subjected to catalytic conversion with a zeolite-containing catalyst, then a carbonaceous deposit may readily form on the surface of the catalyst (coking). Accordingly, during continuous conversion reaction, the catalyst may be degraded by coking (coking degradation), and the catalyst activity may soon lower.

The catalyst of which the catalytic activity has been lowered by coking degradation may be restored to its original catalytic activity generally by heating it in the presence of an oxygen-containing gas to thereby burn away the coke.

However, when the regeneration operation is repeated, then the catalytic activity could not be sufficiently recovered. This is because, in the above regeneration operation, steam is formed through the coke combustion, and when zeolite is heated in the presence of the steam, then aluminium that is an active point of zeolite is released from zeolite crystals and the catalyst thereby undergoes permanent degradation (regeneration degradation).

As in the above, especially coking may often occur in catalytic conversion from an olefin-containing hydrocarbon material with a zeolite-containing catalyst, and therefore frequent regeneration of the catalyst is necessary and regeneration degradation of the catalyst may occur very often.

Patent Document 1 discloses a method of converting a paraffin, an olefin and/or a cycloparaffin (naphthene) having at least 5 carbon atoms into an aromatic hydrocarbon, ethylene and propylene with a proton-type ZSM-5 catalyst. In the method, however, the aromatic hydrocarbon may be obtained at relatively high yield but the yield of ethylene and propylene is low.

Patent Document 2 discloses a method of converting an olefin and a paraffin having from 2 to 4 carbon atoms into an aromatic hydrocarbon, ethylene and propylene with a proton-type ZSM-5 catalyst. Also in the method, the aromatic hydrocarbon may be obtained at relatively high yield but the yield of ethylene and propylene is low.

Patent Documents 3 and 4 disclose a method of converting butene into ethylene and propylene with an aluminophosphate-type molecular sieve. Also in this method, however, the yield of ethylene and propylene is low.

Patent Document 5 discloses a method of producing ethylene and propylene by contacting a hydrocarbon material of a mixture of a paraffin and an olefin having at least 4 carbon atoms and having a specific composition, with a proton-type ZSM5 zeolite. In this method, however, since the degree of conversion is low, a large amount of the unreacted material must be recycled.

Patent Document 6 discloses a method of converting a hydrocarbon having from 3 to 20 carbon atoms into ethylene and propylene with a phosphorus-containing, specific proton-type ZSM5 zeolite. In this method, however, where an olefin is used as the starting material, only the initial performance in 1 minute after the material supply is confirmed.

The characteristic common to the above methods is that a proton-type zeolite is used. In general, the proton-type zeolite has a high acid strength, with which, therefore, ethylene and propylene may be readily successively converted into an aromatic hydrocarbon, and the yield of ethylene and propylene is difficult to increase. In addition, when an olefin-containing hydrocarbon material is used, it often causes coking degradation and regeneration degradation.

Patent Document 7 discloses a proton-free zeolite catalyst that differs from conventional proton-containing zeolite catalysts, and discloses a method of using the catalyst for converting a hydrocarbon material into ethylene, propylene and a monocyclic aromatic hydrocarbon.

The catalyst used in this method is effective in that it hardly undergoes regeneration degradation, but could not still solve the problem of coking degradation. Accordingly, when a hydrocarbon material that contains a large amount of an olefin is processed, then it often causes coking degradation.

Patent Document 8 discloses a method of converting an olefin having from 4 to 12 carbon atoms into ethylene and propylene, with a IB Group metal-containing, aprotic intermediate pore-size zeolite that has a silica/alumina molar ratio of from 200 to 5000.

[Patent Document 1] JP-A-49-41322
[Patent Document 2] JP-A-50-49233
[Patent Document 3] U.S. Pat. No. 4,527,001
[Patent Document 4] U.S. Pat. No. 4,613,721
[Patent Document 5] JP-A-3-27327
[Patent Document 6] JP-A-6-73382
[Patent Document 7] WO1996/013331
[Patent Document 8] WO2000/010948

DISCLOSURE OF THE INVENTION

Problems that the Invention is to Solve

The invention relates to a method for producing ethylene and propylene through catalytic conversion from a hydrocarbon material, more precisely, to a method for producing ethylene and propylene through catalytic conversion from a hydrocarbon material, which comprises contacting a hydrocarbon material that contains at least one olefin having from 4 to 12 carbon atoms in an amount of at least 20% by weight, with a zeolite-containing shaped catalyst in a reactor to thereby produce ethylene and propylene through catalytic conversion of the at least one olefin having from 4 to 12 carbon atoms.

In the technique heretofore proposed, when a proton-type zeolite is used as a catalyst, then ethylene and propylene are readily successively converted into an aromatic hydrocarbon since the catalyst generally has a high acid strength, and therefore it is difficult to improve the yield of ethylene and propylene. In addition, when an olefin-containing hydrocarbon material is used, then it may cause another problem in that coking degradation and regeneration degradation may readily occur.

One example of using an aprotic zeolite proposed recently is Patent Document 8. In its Examples, Patent Document 8 mainly reports a zeolite having a silica/alumina molar ratio ($SiO_2/Al_2O_3$ molar ratio) of 300, and describes also Examples where the silica/alumina molar ratio is 3,000. However, in the Examples with a shaped catalyst having a silica/alumina molar ratio of 300, only the reaction results for a period of up to 24 hours are disclosed. In the Examples where the silica/alumina molar ratio is 3000, only a zeolite powder shaped by compression is used, and the document shows no example of industrially-applicable shaped catalyst formation. In addition, the document is silent at all about the influence of the diolefin concentration in the starting hydrocarbon material on the coking degradation of the catalyst.

The present inventors' studies have revealed the following: Even though the zeolite catalyst disclosed in Patent Document 8, or that is, (1) an intermediate pore-side zeolite having a pore size of from 5 to 6.5 angstroms, (2) which does not substantially contains a proton and (3) which contains at least one metal selected from the group consisting of metals belonging to the Group IB of the Periodic Table, is used, its resistance to coking degradation in industrial working is still insufficient when the zeolite catalyst has a low silica/alumina molar ratio, and therefore the catalyst is problematic in that it requires frequent regeneration and that, when the diolefin compound concentration in the starting hydrocarbon material is high, then the degradation of the catalyst is further more remarkable. Removal of diolefins from the starting material requires pretreatment purification of the starting material such as distillation separation, partial hydrogenation, etc., and it is extremely disadvantageous in industrial working.

On the other hand, when the silica/alumina ratio is high, then it is extremely difficult to make the shaped catalyst support silver through ion exchange, and this is problematic in that the load in catalyst preparation may be large for obtaining an industrially-sufficient catalytic activity.

Means for Solving the Problems

Given that situation, the present inventors extensively studied for the purpose of solving the above problems and, as a result, found that when the silica/alumina ratio in the zeolite to be used for a zeolite shaped catalyst is defined to fall within a specific range, then the catalyst coking degradation and regeneration degradation that are problematic in a process of converting an olefin-containing hydrocarbon material into ethylene and propylene by the use of the zeolite-containing shaped catalyst can be prevented, a hydrocarbon material even though containing diolefins may be directly led to the reaction as it is, and any large load is not needed in catalyst preparation and, as a result, found that ethylene and propylene can be produced stably and efficiently for a long period of time in a simple manner; and we have completed the present invention.

Specifically, the invention is a method for producing ethylene and propylene through catalytic conversion from a hydrocarbon material, as described below.

[1] A method for producing ethylene and propylene by contacting a hydrocarbon material that contains at least one olefin having from 4 to 12 carbon atoms in an amount of at least 20% by weight, with a zeolite-containing shaped catalyst in a reactor for catalytic conversion of the at least one olefin having from 4 to 12 carbon atoms, wherein zeolite in the zeolite-containing shaped catalyst satisfies the following requirements (1), (2), (3) and (4):

(1) the zeolite is an intermediate pore-size zeolite having a pore size of from 5 to 6.5 angstroms,
(2) the zeolite does not substantially contain a proton,
(3) the zeolite contains at least one metal selected from the group consisting of metals belonging to the Group IB of the Periodic Table,
(4) the zeolite has a silica/alumina molar ratio ($SiO_2/Al_2O_3$ molar ratio) of from 800 to 2,000.

[2] The method for producing ethylene and propylene of above [1], wherein the hydrocarbon material contains at least one olefin having from 4 to 12 carbon atoms in an amount of at least 50% by weight relative to the weight of the hydrocarbon material.

[3] The method for producing ethylene and propylene of above [1] or [2], wherein the hydrocarbon material contains at least one diolefin compound having from 3 to 12 carbon atoms in an amount of 2.5% by weight or less relative to the weight of the hydrocarbon material.

[4] The method for producing ethylene and propylene of above [1] to [3], wherein zeolite in the zeolite-containing shaped catalyst supports silver and an alkali metal and does not substantially contain a proton.

[5] The method for producing ethylene and propylene of above [1] to [4], wherein zeolite in the zeolite-containing shaped catalyst is selected from the group consisting of ZSM-5-type zeolites.

[6] The method for producing ethylene and propylene of above [1] to [5], wherein the zeolite-containing shaped catalyst is heat-treated at a temperature not lower than 500° C. in the presence of water vapor, prior to its contact with the hydrocarbon material.

[7] The method for producing ethylene and propylene of above [1] to [6], wherein the reactor is an adiabatic fixed-bed reactor.

[8] The method for producing ethylene and propylene of above [1] to [7], wherein the catalytic conversion conditions are such that the reaction temperature is from 500 to 580° C., the hydrocarbon material partial pressure is from 0.05 to 0.3 MPa, and the weight-hourly space velocity is from 2 to 10 $hr^{-1}$.

ADVANTAGES OF THE INVENTION

According to the zeolite-containing shaped catalyst and the production method of the invention, ethylene and propylene can be efficiently and stably produced from an olefin-based hydrocarbon material. The zeolite-containing shaped catalyst to be used in the method of the invention is highly resistant to degradation, and therefore the products can be produced at high yield and stably for a long period of time in a simple manner. Even though the starting hydrocarbon mixture contains diolefin compounds within a range of not more than 2.5% by weight, it may be directly led to the reaction as it is. Any large load is unnecessary in the catalyst preparation. These characteristics are extremely advantageous in industrially carrying out the invention.

BEST MODE FOR CARRYING OUT THE INVENTION

The invention is described in detail hereinunder.

In the method of the invention, a hydrocarbon material containing at least one olefin having from 4 to 12 carbon atoms in an amount of at least 20% by weight is used as the starting material to produce ethylene and propylene.

In the method of the invention, "hydrocarbon material" represents a starting material essentially containing at least one selected from the group consisting of hydrocarbons having from 1 to 12 carbon atoms, for example, normal paraffins, isoparaffins, olefins, cycloparaffins (naphthenes) and cycloparaffins having a side-chain alkyl group, having from 1 to 12 carbon atoms.

In the method of the invention, the hydrocarbon material contains at least one olefin having from 4 to 12 carbon atoms in an amount of at least 20% by weight relative to the weight of the hydrocarbon material.

The term "olefin" as the constitutive element in the method of the invention is meant to include cycloparaffins in addition to linear, branched and cyclic olefins.

When the olefin content is less than 20% by weight, then the yield of ethylene and propylene may be insufficient. Accordingly, in the method of the invention, the hydrocarbon material contains at least one olefin having from 4 to 12 carbon atoms in an amount of at least 20% by weight, preferably at least 30% by weight, more preferably at least 40% by weight, most preferably at least 50% by weight.

The hydrocarbon material may contain a small amount of oxygen-containing compounds such as tertiary-butanol, methyl tertiary-butyl ether, methanol, as impurities.

The hydrocarbon material for use in the method of the invention may contain diolefin (diene) compounds such as propadiene, butadiene, pentadiene, and acetylene compounds such as methylacetylene, in an amount of 2.5% by weight or less. It is well known that these diolefin compounds are highly polymerizable and may cause coking degradation. Needless-to-say, in general, it is desirable that the diene compounds are reduced to the minimum level through treatment such as distillation separation, partial hydrogenation, but it must be said that such pretreatment is extremely disadvantageous in industrial practice. Surprisingly, however, when the zeolite-containing shaped catalyst of the invention is used, then even a hydrocarbon material containing diolefin compounds may be used as the starting material directly as it is with no pretreatment so far as their concentration is not more than 2.5% by weight, as so mentioned in the above.

Preferred examples of the hydrocarbon material usable in the method of the invention are as follows:

(1) C4 fraction and C5 fraction separated from the product obtained through thermal cracking of petroleum hydrocarbon such as naphtha; and fraction obtained through partial hydrogenation of diolefins in the C4 fraction and C5 fraction into olefins;

(2) Fraction obtained through partial or complete separation and removal of butadiene and isobutene from the C4 fraction;

(3) Fraction obtained through partial or complete separation and removal of isoprene and cyclopentadiene from the C5 fraction;

(4) C4 fraction and gasoline fraction separated from the product obtained through fluid catalytic cracking (FCC) of petroleum hydrocarbon such as reduced-pressure light oil; and (5) C4 fraction and gasoline fraction separated from coker.

One or more of these may be used herein either singly or as combined.

In the method of the invention, the above-mentioned hydrocarbon material is contacted with a specific zeolite-containing shaped catalyst in a reactor to attain catalytic conversion of at least one olefin having from 4 to 12 carbon atoms containing in the hydrocarbon material, thereby obtaining a reaction mixture that contains ethylene and propylene, and ethylene and propylene are separated from the resulting reaction mixture.

In the method of the invention, an "intermediate pore-size zeolite" that has a pore size of from 5 to 6.5 angstroms is used as the zeolite in the zeolite-containing shaped catalyst.

The term "intermediate pore-size zeolite" is meant to indicate "zeolite of which the pore size is intermediate between the pore size of a small pore-size zeolite such as typically A-type zeolite, and the pore size of a large pore-size zeolite such as typically mordenite, or X-type or Y-type zeolite", and this has a 10-membered oxygen ring in the crystal structure thereof.

Examples of the intermediate pore-size zeolite are ZSM-5, ZSM-8, ZSM-11, ZSM-12, ZSM-21, ZSM-23, ZSM-35, ZSM-38. Of those, preferred are ZSM-5-type zeolites such as ZSM-5, ZSM-11, ZSM-8, as well as ZSM-38.

In addition, zeolites similar to ZSM-5 and ZSM-11, as described in P. A. Jacobs and J. A. Martens, *Stud. Surf. Sci. Catal.*, 33, pp. 167-215 (1987, Holland) are also usable herein.

Of those, ZSM-5 is especially preferred.

The zeolite in the zeolite-containing shaped catalyst for use in the method of the invention is one substantially not containing a proton.

"Substantially not containing a proton" as referred to herein for the method of the invention means that the proton amount (acid amount) in the zeolite, as determined according to a liquid-phase ion exchange/filtrate titration method to be mentioned hereinunder, is 0.02 mmol or less per gram of the zeolite. Preferably, the proton amount in the zeolite is 0.01 mmol or less per gram of the zeolite.

The liquid-phase ion exchange/filtrate titration method is described in *Intrazeolite Chemistry*, "ACS Symp. Ser.", 218, pp. 369-382 (1983, USA); *Journal of the Chemical Society of Japan*, [3], pp. 521-527 (1989).

According to the method, the proton amount in the invention may be determined as follows: A zeolite-containing shaped catalyst fired in air is ion-exchanged with an aqueous NaCl solution, and then the zeolite is recovered through filtration and the filtrate is obtained. The recovered zeolite is washed with pure water, and the resulting wash is entirely recovered and combined with the above filtrate. The proton amount in the resulting mixture is obtained through neutralization titration, and this is converted into a unit value per the zeolite weight in the zeolite-containing shaped catalyst, and this value indicates the proton amount in the zeolite.

It is known that ammonium ion-type and polyvalent metal cation-type zeolite (e.g., rare earth metal cation-type zeolite) produces a proton through heat treatment.

Accordingly, prior to the determination of the proton amount according to the above method, the zeolite-containing shaped catalyst must be fired.

The zeolite in the zeolite-containing shaped catalyst for use in the method of the invention is one that contains at least one metal selected from the group consisting of metals belonging to the Group IB of the Periodic Table (hereinafter referred to as "IB Group metal"), or that is, copper, silver, gold. Preferably, the IB Group metal is copper, silver, more preferably silver.

"The Periodic Table" as referred to in the invention is one described in CRC Handbook of Chemistry and Physics, 75th edition [(David R. Lide, et al., published by CRC Press Inc. (1994-1995)], pp. 1-15.

The above "containing a IB Group metal" means that the zeolite contains a IB Group metal as its corresponding cation. However, the IB Group metal may also be in the zeolite in any other state than its cation, in addition to the cation-state metal thereof; and for example, the metal may be therein as its oxide.

One example of incorporating a IB Group metal into zeolite comprises processing a IB Group metal-free zeolite for ordinary ion-exchange treatment. When a IB Group metal is incorporated into zeolite through ion-exchange treatment, a salt of the IB Group metal must be used. The IB Group metal salt includes, for example, silver nitrate, silver acetate, silver sulfate, copper chloride, copper sulfate, copper nitrate, gold chloride.

The amount of the IB Group metal to be in the zeolite-containing shaped catalyst as the IB Group metal cation is not strictly defined, but since the silica/alumina molar ratio of the zeolite for use in the invention is from 800 to 2,000 and since the metal is held through ion exchange, the IB Group metal content shall be naturally determined from the exchange capacity and the zeolite content of the zeolite-containing shaped catalyst. Accordingly, when the amount is expressed in terms of the degree of exchange with the IB Group metal cation relative to the zeolite exchange site and when the degree of exchange is low, then the activity is not sufficient. When the degree of exchange is increased, then the load to the ion exchange and preparation process may be large. In general, therefore, the amount may fall within a range of from 5% to 80%, preferably from 25% to 75%, more preferably from 30% to 70%.

The IB Group metal content of zeolite may be determined in any known method, for example, according to X-ray fluorometric analysis.

As so mentioned in the above, zeolite in the zeolite-containing shaped catalyst in the method of the invention is one not substantially containing a proton, and therefore the ion-exchange site remaining after the IB Group metal cation exchange therein is ion-exchanged with a cation of at least one metal selected from alkali metals and alkaline earth metals. Preferably, it is exchanged with a cation of at least one metal selected from alkali metals, more preferably it is exchanged with a cation of at least one metal selected from the group consisting of sodium and potassium.

Accordingly, the zeolite in the zeolite-containing shaped catalyst in the method of the invention shall contain both at least one metal selected from alkali metals and alkaline earth metals, and a IB Group metal.

For incorporating at least one metal selected from alkali metals and alkaline earth metals into zeolite, employable is a method of ion-exchange treatment to make the corresponding cation held by the zeolite.

The content of at least one metal selected from alkali metals and alkaline earth metals varies depending on the type of the metal, but since the metal is held through ion-exchange treatment, its content shall be naturally determined from the exchange capacity, the zeolite content of the zeolite-containing shaped catalyst and the IB Group metal amount held through ion exchange.

When the zeolite-containing shaped catalyst of the invention is prepared, the order and the frequency of the process of incorporating at least one metal selected from alkali metals and alkaline earth metals into zeolite and the process of incorporating a IB Group metal thereinto are not specifically defined. In any case, however, it is necessary that the metal-incorporated zeolite should not substantially contain a protein, as so mentioned in the above.

For example, in case where the zeolite-containing shaped catalyst of the invention to be prepared is a silver/sodium cation exchange-type one, then a part of silver could not be held as a silver cation when an alkali component exists in the zeolite-containing shaped catalyst; and therefore, the zeolite must be converted into a proton-type one before it is shaped. Accordingly, one preferred method for it is as follows: The zeolite-containing shaped catalyst in which the shaped zeolite is a proton-type zeolite is first converted into a sodium-type one (preferably using an aqueous sodium nitrate solution), and the catalyst is thus converted into a sodium-type one (aprotic one), and thereafter a silver cation is introduced thereinto through ion exchange treatment (preferably using an aqueous silver nitrate solution).

The silica/alumina molar ratio ($SiO_2/Al_2O_3$ molar ratio) in the zeolite in the zeolite-containing shaped catalyst in the method of the invention must be indispensably from 800 to 2,000.

When the silica/alumina molar ratio is less than 800, then the degradation of the zeolite-containing shaped catalyst may be promoted owing to coking after conversion, and for example, when the invention is carried out in a fixed-fed two-tower swing system, then the switching frequency may increase and the regeneration frequency may thereby increase. Accordingly, the speed of the regeneration degradation may also be accelerated. In addition, when the starting hydrocarbon material contains diolefin compounds, the coking degradation may be more remarkable, and the switching frequency may further increase, at last which may therefore interfere with the continuation of safe operation of the method. To evade this, the diolefin compounds in the starting material must be previously processed, and this is disadvantageous in industrially carrying out the invention.

On the other hand, when the silica/alumina molar ratio is more than 2,000, then it may cause a significant problem in catalyst preparation. In order to keep a high catalytic activity of the zeolite-containing shaped catalyst having such a high silica/alumina ratio and in order to prepare the catalyst having a silver content of the same level, the ion-exchange ratio of zeolite must be increased. However, when the zeolite-containing shaped catalyst of the invention is converted into an aprotic, IB Group metal-exchanged one through ion-exchange treatment, then the exchange efficiency lowers with the increase in the ion-exchange ratio.

To evade it, the metal concentration in the exchange solution must be increased. When the silica/alumina molar ratio in zeolite is more than 2,000, then both ion-exchange with alkali metal and ion-exchange with IB Group metal are difficult to promote; and therefore, when the invention is industrially carried out in that condition, then the catalyst preparation takes a lot of time and needs frequent treatments. Another problem with this is that excessive chemical liquids are necessary and therefore the quantity of wastes increases, and this is extremely disadvantageous.

The silica/alumina molar ratio of the zeolite in the zeolite-containing shaped catalyst of the invention is preferably from 900 to 1,800, more preferably from 1,000 to 1,600.

The silica/alumina molar ratio of zeolite may be determined in a known method, for example, by completely dissolving zeolite in an aqueous alkali solution or an aqueous fluoric acid solution, then analyzing the resulting solution through plasma emission spectrometry.

As the zeolite in the zeolite-containing shaped catalyst in the method of the invention, also usable are metalloaluminosilicate in which the aluminium atom constituting the zeolite skeleton is partly substituted with an element of Ga, Fe, B, Cr; and metallosilicate in which the aluminium atom constituting the zeolite skeleton is completely substituted with the above-mentioned element.

In this case, the substituted element content of the metalloaluminosilicate or the metallosilicate is converted into the molar number of alumina, and then the silica/alumina molar ratio of the zeolite is computed.

If desired, the zeolite-containing shaped catalyst in the method of the invention may additionally contain at least one metal selected from the group consisting of metals belonging to Groups IIb, III, Vb, VIIb, VIIb, VIII, such as V, Cr, Me, W, Mn, Pt, Pd, Fe, Ni, Zn, Ga, for the purpose of prevention of coking degradation and for increasing the yield of ethylene and propylene.

The zeolite-containing shaped catalyst in the method of the invention may be heat-treated at a temperature not lower than 500° C. in the presence of water vapor before it is contacted with a hydrocarbon material, for the purpose of further improving its resistance to coking degradation.

The heat treatment conditions are preferably such that the temperature is from 500° C. to 900° C. and the water vapor partial pressure is at least 0.01 atmospheres.

The zeolite-containing shaped catalyst in the method of the invention may undergo coking degradation when used for conversion for a long period of time, but in such a case, in general, the coke on the catalyst may be burnt away in air or in a mixed gas of oxygen and an inert gas, at a temperature of from 400 to 700° C., whereby the catalyst having underwent coking degradation may be regenerated (hereinafter this treatment may be referred to as "regeneration").

The zeolite-containing shaped catalyst in the method of the invention may be produced generally by mixing the above zeolite with a porous refractory inorganic oxide, such as alumina, silica, silica/alumina, zirconia, titania, diatomaceous earth or clay, that serves as a binder or a shaping diluent (matrix), and shaping the resulting mixture, and the thus obtained, shaped product is used as the zeolite-containing shaped catalyst.

When the matrix or binder is used, then its content may be preferably from 10 to 90% by weight of the total weight of zeolite and the matrix or binder, more preferably from 20 to 50% by weight.

In the method of the invention, the above zeolite-containing shaped catalyst is filled in a reactor, in which at least one olefin having from 4 to 12 carbon atoms is processed for catalytic conversion. The catalytic conversion of an olefin having from 4 to 12 carbon atoms is preferably attained under the following condition under which the olefin having from 4 to 12 carbon atoms in the starting hydrocarbon material is converted into ethylene and propylene at high selectivity and the paraffin coexisting in the starting hydrocarbon material does not substantially participate in the reaction. The reaction temperature is preferably from 400 to 600° C., more preferably from 500 to 580° C. The partial pressure of the starting hydrocarbon material is preferably lower, generally from 0.01 to 1 MPa, preferably from 0.05 to 0.3 MPa. The weight hourly space velocity, WHSV, of the hydrocarbon material relative to the weight of the zeolite-containing shaped catalyst is preferably from 1 to 100 $hr^{-1}$, more preferably from 2 to 10 $hr^{-1}$. The contact time between the hydrocarbon material and the zeolite-containing catalyst is preferably 5 seconds shorter, more preferably 1 second or shorter.

The starting hydrocarbon material may be a mixture with a diluent gas. The diluent gas may be an inert gas such as hydrogen, methane, water vapor, nitrogen. Preferably, however, the material does not undergo hydrogen dilution. Specifically, hydrogen may be used for preventing coking degradation of the catalyst, but at the same time it may have some negative influence in that it may hydrogenate the produced propylene to lower the propylene purity (propylene/(propylene+propane)). In the method of the invention, the coking degradation of the catalyst is low and stable operation is possible even though the material is not diluted with hydrogen, and therefore, it is desirable that the material is not diluted with hydrogen.

When the conversion is effected under the condition under which the paraffin does not substantially participate in the reaction, then the olefin conversion in the starting hydrocarbon material is selectively promoted while the paraffin conversion is inhibited with the result that the side production of methane, ethane and propane through paraffin conversion may be prevented, and therefore separation and purification of ethylene and propylene from the reaction mixture may be easy.

In the method of the invention, the reactor in which a starting hydrocarbon material is contacted with the zeolite-containing shaped catalyst may be any of fixed-bed, mobile-bed, fluidized-bed or air-conveyance type reactors.

The zeolite-containing shaped catalyst for use in the method of the invention hardly undergoes coking degradation, and therefore, even though a fixed-bed reactor is used with it, ethylene and propylene may be stably produced therein for a long period of time.

Paraffin conversion is great endothermic reaction, but olefin conversion is slight endothermic reaction or exothermic reaction though varying depending on the reaction condition. Accordingly, when the olefin in the starting hydrocarbon material is selectively reacted under the condition under which the above paraffin does not substantially participate in the reaction, then it is unnecessary to supply reaction heat to the system and therefore a single-stage, adiabatic fixed-bed reactor having a simple structure may be used.

EXAMPLES

The invention is described more concretely with reference to the following Examples and Comparative Examples, to which, however, the invention should not be limited.

Analytical methods employed in Examples and Comparative Examples are as follows:

(1) Proton Determination Through Liquid-Phase Ion-Exchange/Filtrate Titration:

2.5 g of a zeolite-containing shaped catalyst that had been ground in a mortar and burnt in air at a temperature of from 400 to 600° C. is ion-exchanged in 25 ml of an aqueous NaCl solution (3.4 mol/liter) with cooling with ice for 10 minutes. The resulting mixture is filtered, the zeolite is washed with 50 ml of pure water, and all the filtrate including the water used for washing is recovered. The filtrate (including the water used for washing) is neutralized through titration with an aqueous 0.1 N NaOH solution, and the proton amount is obtained from the neutralization point; and from the zeolite content of the zeolite-containing shaped catalyst, the thus-obtained value is converted into a zeolite weight-based proton amount in the sample.

(2) Determination of Silica/Alumina Ratio in Zeolite:

0.2 g of zeolite is added to 50 g of an aqueous 5 N NaOH solution. This is transferred into a stainless microcylinder equipped with a Teflon® inner tube, and the microcylinder is sealed up. This is kept in an oil bath for 15 to 70 hours to completely dissolve the zeolite. The resulting zeolite solution is diluted with ion-exchanged water, and the silicon and aluminium concentration in the diluted liquid is determined with a plasma emission spectrometer (ICP device). From the data, the silica/alumina molar ratio in the zeolite is computed.

ICP Device, and Measurement Condition:

Device: JOBIN YVON (JY138 ULTRACE) by Rigaku Denki

Measurement Condition:

Silicon Measurement Wavelength: 251.60 nm

Aluminium Measurement Wavelength: 396.152 nm

Plasma Power: 1.0 kW

Nebulizer Gas: 0.28 L/min

Sheath Gas: 0.3 to 0.8 L/min

Coolant Gas: 13 L/min (3) Degree of Conversion, Yield:

A degree of conversion (butene-based olefin conversion) is computed according to the following formula:

Degree of Conversion=(C4 to C8 olefin concentration in starting material−butene concentration in product)/(C4 to C8 olefin concentration in starting material).

Ethylene and propylene yield is represented by the ethylene or propylene concentration (% by weight) in the product.

Example 1

An H-exchange-type shaped catalyst that contains a ZSM5-type zeolite having a silica/alumina molar ratio of 1,220 (as measured through ICP by completely dissolving the zeolite-containing shaped catalyst) (containing 30% by weight of $SiO_2$ binder, 1.6 mmφ×5 to 10 mmL) was dispersed in an aqueous 1 N sodium nitrate solution (10 cc/g-shaped zeolite), and subjected to one-hour ion-exchanging treatment repeatedly three times at room temperature. Next, this was filtered, washed with water and dried to prepare an Na-exchange-type ZSM-5/$SiO_2$ shaped catalyst. This was dispersed in an aqueous 0.0017 N silver nitrate solution (10 cc/g-shaped zeolite), and ion-exchanged for 2 hours at room temperature. Next, this was filtered, washed with water and dried to prepare a catalyst A.

The Ag amount in the catalyst A, as determined through X-ray fluorometric analysis, was 0.095% by weight. Specifically, the silver cation population (ion exchange ratio) relative to the zeolite exchange site (aluminium amount) was 46.2%.

The catalyst A was filled in a hastelloy C reactor having an inner diameter of 27.2 mmφ, and steamed for 5 hours under the condition of a temperature of 650° C., a steam flow rate of 218 g/hr, and a nitrogen flow rate of 220 NL/hr.

After steamed, the proton amount in the catalyst A was determined through liquid-phase ion-exchange/filtrate titration according to the above method, and was 0.0014 mmol/q-zeolite.

60 g of the seamed catalyst A was filled in a hastelloy C reactor having an inner diameter of 27.2 mmφ.

C4 raffinate-2 (obtained through steam cracking of naphtha followed by extraction of butadiene and isobutene from the resulting C4 fraction), No. 1 as in Table 1 was used as the starting material. This was processed under the condition of a reaction temperature of 550° C., a C4 raffinate-2 supply rate of 450 g/hr (WHSV=7.50 $hr^{-1}$), and 0.1 MPaG.

The reaction product in a predetermined period of time after the start of the supply of the starting material was directly led into a gas chromatographic analyzer (TCD, FID detector) from the outlet port of the reactor, and analyzed for its composition.

The gas chromatographic analysis was under the following condition.

(Gas Chromatographic Analysis Condition),

Device: Shimadzu's GC-17A,

Column: US SUPELCO's custom capillary column SPB-1 (inner diameter 0.25 mm, length 60 m, film thickness 3.0 μm), Sample Gas Amount: 1 ml (sampling line was kept warmed at 200 to 300° C.), Heating Program Kept at 40° C. for 12 minutes, then heated up to 200° C. at a rate of 5° C./min, and then kept at 200° C. for 22 minutes, Split Ratio: 200/1, Carrier Gas (nitrogen) Flow Rate: 120 ml/min, FID Detector: air supply pressure 50 kPa (about 500 ml/min), hydrogen supply pressure 60 kPa (about 50 ml/min), Measurement Method: TCT detector and FID detector are connected in series, and hydrogen and C1 and C2 hydrocarbons are detected with TCD detector, and hydrocarbons of C3 or more are detected with FID detector. 10 minutes after the start of the analysis, the detection output is switched from TCD to FID.

Suitably analyzing the reaction product, the reaction was continued for 48 hours. The results are shown in Table 2 and FIG. 1.

The propylene yield difference between 2 hours and 48 hours after the start of the reaction in this Example [PY yield (2 hours)−PY yield (48 hours)] was kept only 2%.

From this Example and Comparative Example 1, it is known that, when the silica/alumina ratio in zeolite in the zeolite-containing shaped catalyst was 400, then the PY yield greatly lowered in running operation for 2 days owing to the coking degradation of the catalyst, but when zeolite having a silica/alumina ratio of 1,220 was used, then the reduction in the propylene yield in running operation for 2 days was kept only 2%. Specifically, in case where the invention is industrially carried out according to a simple two-tower swing system with fixed-bed reactors, then the yield fluctuation in catalyst switching is small (on an acceptable level in running maintenance) even in a 2-day cycle where the catalyst of the invention is used, and this suggest the possibility of two-day cycle operation with the catalyst of the invention.

Example 2

The same reaction experiment as in Example 1 was carried out, in which, however, C4 raffinate-2, No. 2 was used as the starting material to be fed to the reactor. C4 raffinate-2, No. 2 contains diolefin compounds (methylacetylene, propadiene, butadiene) in an amount of 2.25% by weight.

Figure 1:
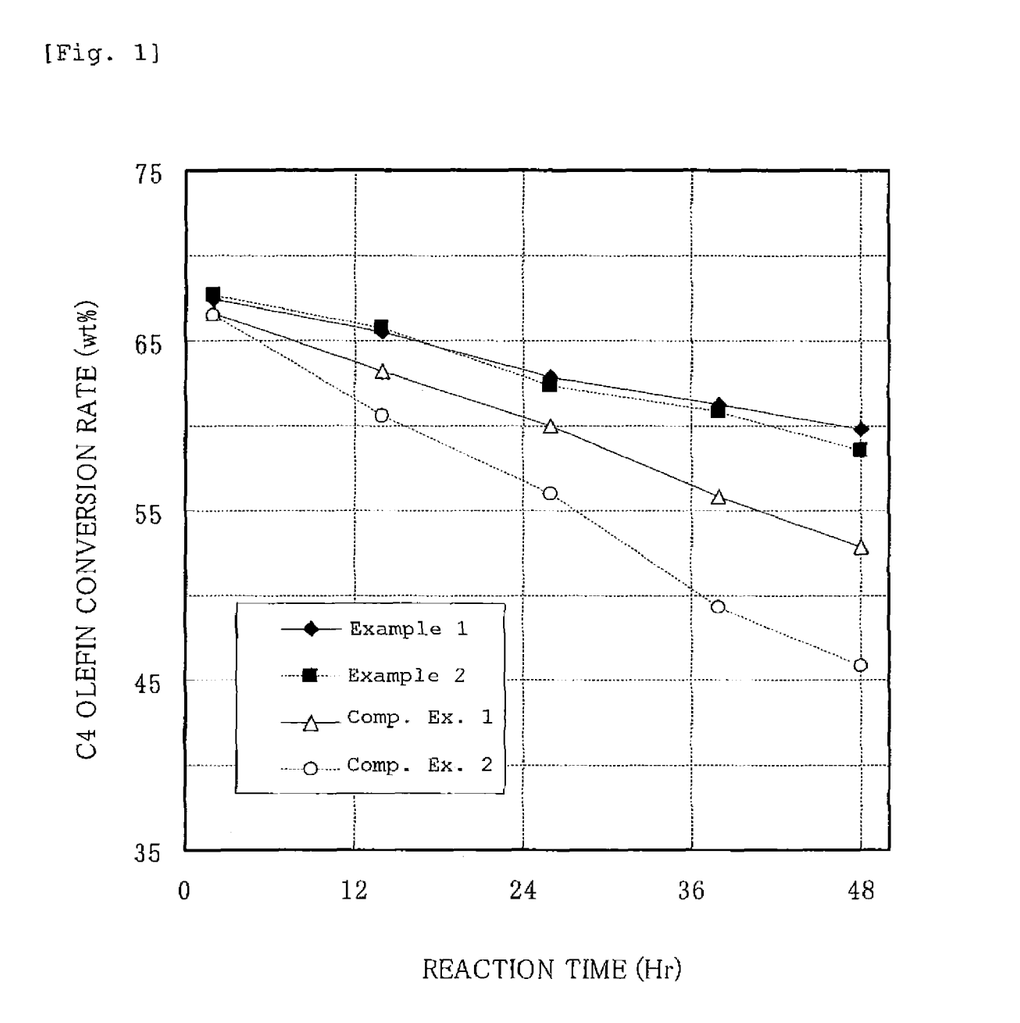
FIG. 1 It is a graph showing the changes of C4 olefin conversion with time in Examples 1 and 2 of the invention and in Comparative Examples 1 and 2.

The reaction results are shown in Table 2, and FIG. 1.

The propylene yield difference between 2 hours and 48 hours after the start of the reaction was 2.56%. From this Example and Comparative Example 2, it is known that, even though a starting material that has a diolefin compound concentration of 2.25% by weight is used, it has no negative influence on the activity of the zeolite-containing shaped catalyst of the invention used, and two-day running operation is possible with no practical problem.

Comparative Example 1

An H-exchange-type shaped catalyst that contains a ZSM5-type zeolite having a silica/alumina molar ratio of 410 (as measured through ICP by completely dissolving the zeolite-containing shaped catalyst) (containing 30% by weight of $SiO_2$ binder, 1.6 mm$\phi$×5 to 10 mL) was dispersed in an aqueous 1 N sodium nitrate solution (10 cc/g-shaped zeolite), and subjected to one-hour ion-exchanging treatment repeatedly three times at room temperature. Next, this was filtered, washed with water and dried to prepare an Na-exchange-type ZSM-5/$SiO_2$ shaped catalyst. This was dispersed in an aqueous 0.00145 N silver nitrate solution (10 cc/g-shaped zeolite), and ion-exchanged for 2 hours at room temperature. Next, this was filtered, washed with water and dried to prepare a catalyst B.

The Ag amount in the catalyst B, as determined through X-ray fluorometric analysis, was 0.094% by weight. Specifically, the silver cation population (ion exchange ratio) relative to the zeolite exchange site (aluminium amount) was 15.3%.

The catalyst B was filled in a hastelloy C reactor having an inner diameter of 27.2 mm$\phi$, and steamed for 5 hours under the condition of a temperature of 650° C., a steam flow rate of 218 g/hr, and a nitrogen flow rate of 220 NL/hr.

After steamed, the proton amount in the catalyst B was determined in the same manner as in Example 1, and was 0.0016 mmol/g-zeolite.

The steamed catalyst B was tested and evaluated in the same manner as in Example 1. The results are shown in Table 3 and FIG. 1. The propylene yield difference between 2 hours and 48 hours after the start of the reaction in this Comparative Example was 4.6% and was relatively large.

Comparative Example 2

The same reaction experiment as in Comparative Example 1 was carried out, in which, however, C4 raffinate-2, No. 2 was used as the starting material to be fed to the reactor. The results are shown in Table 3, and FIG. 1.

The propylene yield difference between 2 hours and 48 hours after the start of the reaction in this Comparative Example was 8%, and the reduction in the propylene yield was remarkable.

Example 3

An H-exchange-type shaped catalyst that contains a ZSM5-type zeolite having a silica/alumina molar ratio of 1,840 (as measured through ICP by completely dissolving the zeolite-containing shaped catalyst) (containing 30% by weight of $SiO_2$ binder, 1.6 mm$\phi$×5 to 10 mL) was dispersed in an aqueous 1 N sodium nitrate solution (10 cc/g-shaped zeolite), and subjected to one-hour ion-exchanging treatment repeatedly three times at room temperature. Next, this was filtered, washed with water and dried to prepare an Na-exchange-type ZSM-5/$SiO_2$ shaped catalyst. This was dispersed in an aqueous 0.0026 N silver nitrate solution (10 cc/g-shaped zeolite), and ion-exchanged for 2 hours at room temperature. Next, this was filtered, washed with water and dried to prepare a catalyst C.

Similarly, an H-exchange-type shaped catalyst that contains a ZSM5-type zeolite having a silica/alumina molar ratio of 850 (containing 30% by weight of $SiO_2$ binder, 1.6 mm$\phi$×5 to 10 mL) was Na-exchanged, then Ag-exchanged, filtered, washed with water and dried to prepare a catalyst D.

However, the concentration of the aqueous silver nitrate solution was 0.0016 N.

As measured through X-ray fluorometric analysis, the Ag amount in the catalyst C was 0.094% by weight, and the Ag amount in the catalyst D was 0.093% by weight. Specifically, the silver cation population (ion exchange ratio) relative to the zeolite exchange site (aluminium amount) was 69% in the catalyst C, and was 31.5% in the catalyst D.

Like in Example 1, the catalysts C and D were filled in a hastelloy C reactor having an inner diameter of 27.2 mm$\phi$, and steamed for 5 hours under the condition of a temperature of 650° C., a steam flow rate of 218 g/hr, and a nitrogen flow rate of 220 NL/hr.

After steamed, the proton amount in the catalyst C was 0.0014 mmol/g-zeolite, and was 0.0015 mmol/g-zeolite in the catalyst D.

In the same manner as in Examples 1 and 2, the steamed catalysts C and D were tested and evaluated. The results are shown in Table 4.

Comparative Example 3

An H-exchange-type shaped catalyst that contains a ZSM5-type zeolite having a silica/alumina molar ratio of 2,300 or 3,000 (as measured through ICP by completely dissolving the zeolite-containing shaped catalyst) (containing 30% by weight of $SiO_2$ binder, 1.6 mm$\phi$×5 to 10 mL) was dispersed in an aqueous 1 N sodium nitrate solution (10 cc/g-shaped zeolite), and subjected to one-hour ion-exchanging treatment repeatedly three times at room temperature. Next, this was filtered, washed with water and dried to prepare an Na-exchange-type ZSM-5/$SiO_2$ shaped catalyst. This was dispersed in an aqueous 0.01 N silver nitrate solution (10 cc/g-shaped zeolite), and ion-exchanged for 2 hours at room temperature. Next, this was filtered, washed with water and dried to prepare a catalyst E (silica/alumina ratio 2300), and a catalyst F.

As measured through X-ray fluorometric analysis, the Ag amount in the catalyst E was 0.084% by weight, and the Ag amount in the catalyst F was 0.044% by weight. Specifically, the silver cation population (ion exchange ratio) relative to the zeolite exchange site (aluminium amount) was 77% in the catalyst E, and was 53% in the catalyst F.

Like in Example 1, the catalysts E and F were filled in a hastelloy C reactor having an inner diameter of 27.2 mm$\phi$, and steamed for 5 hours under the condition of a temperature of 650° C., a steam flow rate of 218 g/hr, and a nitrogen flow rate of 220 NL/hr.

After steamed, the proton amount in the catalyst E and in the Catalyst F was 0.0014 mmol/g-zeolite.

In the same manner as in Examples 1 and 2, the steamed catalysts E and F were tested and evaluated.

With the catalyst E, the C4 olefin conversion in 2 hours was 60.4% and the propylene yield was 20.7%; the C4 olefin conversion in 48 hours was 47.8% and the propylene yield was 16.4%. For the catalyst E, the silver ion-exchanging liquid concentration was increased, but the catalyst could not have a desired level of the exchanged silver amount, and its initial activity was low. The activity reduction in 48 hours was large.

On the other hand, with the catalyst F, the C4 olefin conversion in 2 hours was 32% and was extremely low. Therefore, continuation of the reaction was stopped. In the catalyst F, even though the silver cation population could be 100% relative to the zeolite exchange site, the silver content of the catalyst could be only at most 0.083 by weight. Naturally, it could be readily presumed that the activity of the catalyst is low. However, even though the silver ion-exchanging liquid concentration was increased, the exchanged silver amount in the catalyst could not still reach a half of the desired level, and the activity of the catalyst was extremely low.

From this Comparative Example, it is known that, even though the silver-exchanging liquid concentration is increased in the process of preparing a zeolite-containing shaped catalyst in which the zeolite has a silica/alumina ratio of more than 2000, the catalyst could not have a sufficient amount of silver as its ion-exchanging efficiency is low. When the catalyst of the type is used in reaction, obviously it could not exhibit sufficient activity.

TABLE 1

| Ingredient | C4 Raffinate-2 No. 1 | C4 Raffinate-2 No. 2 |
| --- | --- | --- |
| Methylacetylene | 0.01 | 0.02 |
| Propadiene | 0.10 | 0.12 |
| Propylene | 0.06 | 0.06 |
| Propane | 0.05 | 0.05 |
| Butadiene | 1.14 | 2.12 |
| Butene | 76.92 | 76.46 |
| Butane | 21.02 | 20.57 |
| Pentene | 0.25 | 0.22 |
| Pentane | 0.23 | 0.20 |
| Benzene | 0.00 | 0.00 |
| C6 Non-aromatic Hydrocarbon | 0.01 | 0.01 |
| Toluene | 0.02 | 0.02 |
| C7 Non-aromatic Hydrocarbon | 0.17 | 0.15 |
| C8 Aromatic Hydrocarbon | 0.00 | 0.00 |
| C8 Non-aromatic Hydrocarbon | 0.02 | 0.01 |
| C9+ Hydrocarbon | 0.01 | 0.01 |
| Total | 100.0 | 100.00 |
| Diolefin Compounds | 1.26 | 2.25 |

TABLE 2

| | | | | | | |
| --- | --- | --- | --- | --- | --- | --- |
| Example 1 Catalyst A | Silica/Alumina Molar Ratio | 1220 | | | | |
| | Silver Content (wt. %) | 0.095 | | | | |
| | Starting Material | No. 1 | | | | |
| | Reaction Time | 2 | 14 | 26 | 38 | 48 |
| | C4 Olefin Conversion (wt. %) | 67.45 | 65.51 | 62.89 | 61.28 | 59.81 |
| | Ethylene Yield (wt. %) | 4.58 | 4.03 | 3.59 | 3.30 | 3.02 |
| | Propylene Yield (wt. %) | 22.34 | 22.00 | 21.30 | 20.74 | 20.34 |
| Example 1 Catalyst B | Silica/Alumina Molar Ratio | 1220 | | | | |
| | Silver Content (wt. %) | 0.095 | | | | |
| | Starting Material | No. 2 | | | | |
| | Reaction Time | 2 | 14 | 26 | 38 | 48 |
| | C4 Olefin Conversion (wt. %) | 67.70 | 65.73 | 62.37 | 60.87 | 58.52 |
| | Ethylene Yield (wt. %) | 4.49 | 4.13 | 3.45 | 3.23 | 2.81 |
| | Propylene Yield (wt. %) | 22.48 | 22.03 | 21.20 | 20.61 | 19.92 |

TABLE 3

| | | | | | | |
| --- | --- | --- | --- | --- | --- | --- |
| Comparative Example 1 Catalyst B | Silica/Alumina Molar Ratio | 410 | | | | |
| | Silver Content (wt. %) | 0.094 | | | | |
| | Starting Material | No. 1 | | | | |
| | Reaction Time | 2 | 14 | 26 | 38 | 48 |
| | C4 Olefin Conversion (wt. %) | 66.63 | 63.22 | 60.00 | 55.82 | 52.91 |
| | Ethylene Yield (wt. %) | 4.17 | 3.55 | 3.02 | 2.43 | 2.08 |
| | Propylene Yield (wt. %) | 22.42 | 21.53 | 20.54 | 19.02 | 17.81 |
| Comparative Example 2 Catalyst B | Silica/Alumina Molar Ratio | 410 | | | | |
| | Silver Content (wt. %) | 0.094 | | | | |
| | Starting Material | No. 2 | | | | |
| | Reaction Time | 2 | 14 | 26 | 38 | 48 |
| | C4 Olefin Conversion (wt. %) | 66.50 | 60.55 | 56.01 | 49.33 | 45.83 |
| | Ethylene Yield (wt. %) | 4.14 | 3.11 | 2.46 | 1.72 | 1.44 |
| | Propylene Yield (wt. %) | 22.38 | 20.72 | 19.09 | 16.14 | 14.32 |

TABLE 4

| | | | | | |
| --- | --- | --- | --- | --- | --- |
| Example 3 Catalyst C | Silica/Alumina Molar Ratio | 1840 | | | |
| | Silver Content (wt. %) | 0.094 | | | |
| | Starting Material | No. 1 | | No. 2. | |
| | Reaction Time | 2 | 48 | 2 | 48 |
| | C4 Olefin Conversion (wt. %) | 66.76 | 59.11 | 67.24 | 59.08 |
| | Ethylene Yield (wt. %) | 4.19 | 2.89 | 4.52 | 2.90 |
| | Propylene Yield (wt. %) | 22.44 | 20.24 | 22.37 | 19.94 |
| Example 3 Catalyst D | Silica/Alumina Molar Ratio | 850 | | | |
| | Silver Content (wt. %) | 0.093 | | | |
| | Starting Material | No. 1 | | No. 2 | |
| | Reaction Time | 2 | 48 | 2 | 48 |
| | C4 Olefin Conversion (wt. %) | 67.68 | 59.31 | 67.19 | 58.79 |
| | Ethylene Yield (wt. %) | 4.63 | 6.01 | 4.54 | 2.95 |
| | Propylene Yield (wt. %) | 22.36 | 20.13 | 22.28 | 19.86 |

While the present invention has been described in detail and with reference to specific embodiments thereof, it will be apparent to one skilled in the art that various changes and modifications can be made therein without departing from the spirit and scope thereof.

This application is based on Japanese Patent Application Nos. 2005-270322 (filed Sep. 16, 2005) and 2005-360230 filed Dec. 14, 2005, the entire contents thereof being herein incorporated by reference.

INDUSTRIAL APPLICABILITY

In a method for producing ethylene and propylene through catalytic conversion from a hydrocarbon material, in which a hydrocarbon material that contains at least one olefin having from 4 to 12 carbon atoms in an amount of at least 20% by weight is contacted with a zeolite-containing shaped catalyst in a reactor to attain catalytic conversion of the at least one olefin having from 4 to 12 carbon atoms to produce ethylene and propylene, when the zeolite-containing shaped catalyst of the invention is used, then ethylene and propylene can be produced efficiently and stably. This is because the zeolite-containing shaped catalyst to be used in the method of the invention is extremely highly resistant to deterioration, and therefore the products can be stably produced at high yield for a long period of time in a simple manner. Even though the starting hydrocarbon mixture contains diolefin compounds within a range of not more than 2.5% by weight, it may be directly led to the reaction as it is. Any large load is unnecessary in the catalyst preparation. These characteristics are extremely advantageous in industrially carrying out the invention.

The invention claimed is:

1. A method for producing ethylene and propylene by contacting a hydrocarbon material that contains at least one olefin having from 4 to 12 carbon atoms in an amount of at least 20% by weight, with a zeolite-containing shaped catalyst in a reactor for catalytic conversion of the at least one olefin having from 4 to 12 carbon atoms, wherein zeolite in the zeolite-containing shaped catalyst satisfies the following requirements (1), (2), (3) and (4):
   (1) the zeolite is an intermediate pore-size zeolite having a pore size of from 5 to 6.5 angstroms,
   (2) the zeolite does not substantially contain a proton,
   (3) the zeolite contains at least one metal selected from the group consisting of metals belonging to the Group IB of the Periodic Table,
   (4) the zeolite has a silica/alumina molar ratio ($SiO_2/Al_2O_3$ molar ratio) of from 800 to 2,000.

2. The method for producing ethylene and propylene as claimed in claim 1, wherein the hydrocarbon material contains at least one olefin having from 4 to 12 carbon atoms in an amount of at least 50% by weight relative to the weight of the hydrocarbon material.

3. The method for producing ethylene and propylene as claimed in claim 1, wherein the hydrocarbon material contains at least one diolefin compound having from 3 to 12 carbon atoms in an amount of 2.5% by weight or less relative to the weight of the hydrocarbon material.

4. The method for producing ethylene and propylene as claimed in claim 1, wherein zeolite in the zeolite-containing shaped catalyst supports silver and an alkali metal and does not substantially contain a proton.

5. The method for producing ethylene and propylene as claimed in claim 1, wherein zeolite in the zeolite-containing shaped catalyst is selected from the group consisting of ZSM-5, ZSM-8, ZSM-11, ZSM-12, ZSM-21, ZSM-23, ZSM-35 and ZSM-38 zeolites.

6. The method for producing ethylene and propylene as claimed in claim 1, wherein the zeolite-containing shaped catalyst is heat-treated at a temperature not lower than 500° C. in the presence of water vapor, prior to its contact with the hydrocarbon material.

7. The method as claimed in claim 1, wherein the reactor is an adiabatic fixed-bed reactor.

8. The method for producing ethylene and propylene as claimed in claim 1, wherein the catalytic conversion conditions are such that the reaction temperature is from 500 to 580° C., the hydrocarbon material partial pressure is from 0.05 to 0.3 MPa, and the weight-hourly space velocity is from 2 to 10 $hr^{-1}$.

9. The method for producing ethylene and propylene as claimed in claim 1 or 3, wherein the hydrocarbon material contains at least one diolefin compound having from 3 to 12 carbon atoms in an amount of 1.14% or more by weight or more relative to the weight of the hydrocarbon material.

* * * * *